United States Patent [19]
Jendrisak et al.

[11] Patent Number: 5,459,055
[45] Date of Patent: * Oct. 17, 1995

[54] **THERMOSTABLE RIBONUCLEASE H ISOLATED FROM *THERMUS FLAVUS***

[75] Inventors: Jerome J. Jendrisak; Robert E. Smith; Gary A. Dahl, all of Madison, Wis.

[73] Assignee: Epicentre Technologies Corporation, Madison, Wis.

[ * ] Notice: The portion of the term of this patent subsequent to Dec. 7, 2010 has been disclaimed.

[21] Appl. No.: 163,181

[22] Filed: Dec. 6, 1993

Related U.S. Application Data

[63] Continuation-in-part of Ser. No. 815,095, Dec. 27, 1991, Pat. No. 5,268,289.

[51] Int. Cl.$^6$ .............................. C12N 9/14; C12N 9/16; C12N 9/22
[52] U.S. Cl. .................... 435/199; 435/183; 435/195; 435/196
[58] Field of Search .................... 435/199, 183, 435/195, 196

[56] References Cited

U.S. PATENT DOCUMENTS

| | | | |
|---|---|---|---|
| 3,896,000 | 7/1975 | Kamekura et al. | 435/196 |
| 4,889,818 | 12/1989 | Gelfand et al. | 435/194 |
| 5,268,289 | 12/1993 | Dahl et al. | 435/199 |

FOREIGN PATENT DOCUMENTS

| | | |
|---|---|---|
| 2057181 | 2/1990 | Japan . |
| 1495377 | 7/1989 | U.S.S.R. . |

OTHER PUBLICATIONS

Itaya, et al., "Molecular cloning of a ribonuclease H (RNase HI) gene from an extreme thermophile *Thermus thermophilus* HB8: A thermostable RNase H can functionally replace the *Escherichia coli* enzyme in vivo", *Nucl. Acids Res.* 19(16):4443–4449, 1991.

Kanaya, et al., "Expression, Purification, and Characterization of a Recombinant Ribonuclease H from *Thermus thermophilus* HB8*", *The Jour. of Biol. Chem.* (14):10184–10192, 1992.

Crouch, R. et al. "Ribonucleases H" In *Nuclease* (1982) (Levin, S. M., and Roberts, R. J. Eds) pp. 211–241, Cold Spring Harbor Laboratory, Cold Spring Harbor, New York.

Kanaya, S. et al. "DNA Sequence of the Gene Coding for *Eschericha coli* Ribonuclease H," *J. Biol. Chem.*, 258[2]: 1276–1281 (1983).

Berkower, I., et al., "Isolation and Characterization of an Endonuclease from *Escherichia coil* Specific for Ribonucleic Acid in Ribonucleic Acid Deoxyribonucleic Acid Hybrid Structures," *J. Biol. Chem.*, 248[17]: 5914–5921 (1973).

Gubler U., et al., "A simple and very efficient method for generating cDNA libraries," *Gene* 25: 263–269 (1983).

Guatelli, J. C. et al. "Isothermal, in vitro amplication of nucleic acids by a multienzyme reaction modeled after retroviral replication," *Proc. Natl. Acad. Sci. USA*, 87: 1874–1878 (1990).

Kuze, et al., "A new vector and RNase H method for the subtractive hybridization," *Nucleic Acids Res.*, 17[2]: 807 (1989).

Minshull, J., et al., "The use of single–stranded DNA and RNase H to promote quantitative 'hybrid arrest of translation' of mRNA/DNA hybrids in reticulocyte lysate cell–free translations," *Nucleic Acids Res.*,14[16]: 6433–6451 (1986).

Krug, M. S. et al., "Determination of the Molar Concentration of Messenger RNA", *Methods in Enzymology*, 152: 262–317 (1987).

Duck, P. et al., "Probe Amplifier System Based on Chimeric Cycling Oligonucleotides," *Biotechniques*, 9[2]: 142 (1990).

Crouch, R., in *Gene Amplification and Analysis* (1981) (Cherikjian, J. G., and Popas, T. S., eds) 2: 217–228, Elsewier, North Holland, New York.

Okayama, H., et al. "High–Efficiency Cloning of Full–Length cDNA," *Mol. Cell. Biol.* 2[2]: 161–170 (1982).

Jendrisak, J. "The use of Polyethyleneimine in Protein Purification," Protein Purification: Micro to Macro, pp. 75–97 (1987).

Lawyer, F. C. et al., "Isolation, Characterization, and Expression in *Escherichia coli* of the DNA Polymerase Gene from *Thermus aquaticus*," *J. Biol. Chem.*, 264 ]11]: 6427–6437 (1989).

*Primary Examiner*—David M. Naff
*Assistant Examiner*—L. Blaine Lankford
*Attorney, Agent, or Firm*—Quarles & Brady

[57] ABSTRACT

An essentially pure preparation of thermostable RNase H isolated from Thermus flavus is disclosed. In one preferable form of the invention, the RNase H is capable of biological activity after incubation at temperatures equal to or greater than 70° C. for at least ten minutes. The present invention is also a method of digesting RNA polymers that are in duplex form with a DNA molecule. The method comprises exposing the duplex to the isolated thermostable RNase H. The present invention is also a genetic construct capable of expressing a thermostable RNase H.

2 Claims, 6 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( D ) TOPOLOGY: linear     ( i i ) MOLECULE TYPE: protein     ( v ) FRAGMENT TYPE: N-terminal     ( v i ) ORIGINAL SOURCE:
        ( A ) ORGANISM: Thermus thermophilus
        ( B ) STRAIN: HB-8

( x i ) SEQUENCE DESCRIPTION: SEQ ID NO:1:

```
Met  Asn  Pro  Ser  Pro  Arg  Lys  Arg  Val  Ala  Leu  Phe
1              5                        10

Thr  Asp  Gly  Ala  Cys  Leu  Gly  Asn  Pro  Gly  Pro  Gly
          15                       20

Gly  Cys  Ala  Arg  Leu  Leu  Arg  Phe  Lys  Ala
25                       30
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( D ) TOPOLOGY: linear     ( i i ) MOLECULE TYPE: protein     ( v ) FRAGMENT TYPE: N-terminal     ( v i ) ORIGINAL SOURCE:
        ( A ) ORGANISM: Escherichia coli     ( x ) PUBLICATION INFORMATION:
        ( A ) AUTHORS: Ranaya, S.
        ( C ) JOURNAL: J. Biol. Chem.
        ( D ) VOLUME: 258
        ( F ) PAGES: 1276-1281
        ( G ) DATE: 1983

( x i ) SEQUENCE DESCRIPTION: SEQ ID NO:2:

```
Met  Leu  Lys  Gln  Val  Glu  Ile  Phe  Thr  Asp  Gly  Ser  Cys
1                   5                        10

Leu  Gly  Asn  Pro  Gly  Pro  Gly  Gly  Tyr  Gly  Ala  Ile  Leu
          15                       20                       25

Arg  Tyr  Arg  Gly
               30
```

( 2 ) INFORMATION FOR SEQ ID NO:3:

( i ) SEQUENCE CHARACTERISTICS:
        ( A ) LENGTH: 501 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:3:

```
GTGAACCCCT CCCCCAGGAA ACGCGTGGCC CTCTTCACCG ACGGGCCTG  CCTGGGAAAC    60
CCCGGGCCCG GGGGGTGGGC GGCCCTCCTC CGCTTCCACG CCCACGAGAA GCTCCTCTCC   120
GGGGGAGAGG CCTGCACCAC CAACAACCGC ATGGAGCTCA AGGCGGCCAT AGAGGGCCTA   180
AAGGCCCTCA AGGAGCCTTG CGAGGTGGAC CTCTACACCG ACAGCCACTA CCTCAAGAAG   240
GCCTTCACCG AGGGCTGGCT GGAAGGCTGG CGGAAAAGGG GCTGGCGGAC GGCGGAGGGC   300
AAGCCCGTGA AAAACCGCGA CCTCTGGGAG GCCCTCCTCC TCGCCATGGC CCCCCACCGG   360
GTGCGCTTCC ACTTCGTGAA GGGGCACACG GGCCACCCGG AGAACGAACG GGTGGACCGG   420
GAGGCGAGGC GCCAGGCCCA GTCCCAGGCC AAAACGCCCT GCCCGCCCCG GGCCCCCACG   480
CTTTTCCACG AAGAGGCATA A                                            501
```

( 2 ) INFORMATION FOR SEQ ID NO:4:

( i ) SEQUENCE CHARACTERISTICS:
        ( A ) LENGTH: 552 base pairs ( B ) TYPE: nucleic acid
( C ) STRANDEDNESS: double
( D ) TOPOLOGY: linear ( i i ) MOLECULE TYPE: Other Nucleic Acid ( x i ) SEQUENCE DESCRIPTION: SEQ ID NO:4:

| | | | | | | |
|---|---|---|---|---|---|---|
| ATGATTACGA | ATTCGAGCTC | GGTACCCGGG | GATCTGGGGC | CTGGAGGAGG | CGTGAACCCC | 60 |
| TCCCCCAGGA | AACGCGTGGC | CCTCTTCACC | GACGGGGCCT | GCCTGGGAAA | CCCCGGGCCC | 120 |
| GGGGGGTGGG | CGGCCCTCCT | CCGCTTCCAC | GCCCACGAGA | AGCTCCTCTC | CGGGGGAGAG | 180 |
| GCCTGCACCA | CCAACAACCG | CATGGAGCTC | AAGGCGGCCA | TAGAGGGCCT | AAAGGCCCTC | 240 |
| AAGGAGCCTT | GCGAGGTGGA | CCTCTACACC | GACAGCCACT | ACCTCAAGAA | GGCCTTCACC | 300 |
| GAGGGCTGGC | TGGAAGGCTG | GCGGAAAAGG | GGCTGGCGGA | CGGCGGAGGG | CAAGCCCGTG | 360 |
| AAAAACCGCG | ACCTCTGGGA | GGCCCTCCTC | CTCGCCATGG | CCCCCACCG | GGTGCGCTTC | 420 |
| CACTTCGTGA | AGGGGCACAC | GGGCCACCCG | GAGAACGAAC | GGGTGGACCG | GGAGGCGAGG | 480 |
| CGCCAGGCCC | AGTCCCAGGC | CAAAACGCCC | TGCCCGCCCC | GGGCCCCCAC | GCTTTTTCAC | 540 |
| GAAGAGGCAT | AA | | | | | 552 |

THERMOSTABLE RIBONUCLEASE H ISOLATED FROM *THERMUS FLAVUS*

RELATED APPLICATION INFORMATION

This application is a continuation-in-part of U.S. Ser. No. 07/815,095, filed Dec. 27, 1991.

FIELD OF THE INVENTION

The present invention relates to the field of molecular biology. More specifically, the present invention relates to the creation and use of the enzyme thermostable ribonuclease H.

BACKGROUND OF THE INVENTION

Ribonuclease H (endoribonuclease H, EC 5.1.26.4, hereafter referred to as RNase H) is an enzyme capable of hydrolyzing an RNA molecule when the RNA molecule is hybridized with a complementary DNA strand. The biological role of the enzyme is not known. Hence it is not known whether all organisms possess this enzyme.

RNase H is a useful tool in molecular biology research. RNase H is used for degrading the RNA strand after first-strand synthesis in the production of double-stranded cDNA. Okayama, H., et al. (1982) *Mol. Cell. Biol.* 2:161–170.6; Gubler, U., et al. (1983) *Gene* 25:263–269. The enzyme can remove poly-(A) tails from messenger RNA if the mRNA is reacted with oligo-dT$_{12-18}$. Vournakis, J., et al. (1975) *Proc. Natl. Acad. Sci. USA* 72:2959–2963; Davis, R., et al. (1988) *Mol. Cell. Biol.* 8:4745–4755.

Most importantly, RNase H is used as a diagnostic tool for detecting specific target DNA sequences in a biological sample by a probe amplification process. Duck, P., et al. (1990) *BioTechniques* 9:142–147. In this diagnostic technique, a probe is made of ribonucleoside bases flanked by deoxy-ribonucleoside bases. The probe hybridizes to a target DNA molecule. RNase H digests the ribonucleoside bases and cleaves the probe. The probe fragments then dissociate from the target. After many cycles, these fragments accumulate and serve as a basis for detecting the presence of the target.

RNase H is a component of another diagnostic test called the self-sustained sequence replication (3SR) amplification system, which is a transcription-based amplification method. Guatelli, J. C., et al. (1990) *Proc. Natl. Acad. Sci. USA* 87:1874–1878. In the 3SR system, a target nucleic acid sequence is replicated exponentially by using RNase H, a DNA-dependent RNA polymerase and reverse transcriptase.

RNase H may also be used to map the location of sequences on an RNA molecule. First the RNA is annealed with specific oligodeoxyribonucleotide probes and then the duplexed RNA is cleaved with RNase H. Donis-Keller, H. (1979) *Nucleic Acids Res.* 7:179–192.

RNase H may also be used to quantitate poly-(A)-containing mRNA in biological samples. Krug, M. S., et al. (1987) *Methods Enzymol.* 152:262–266. RNase H is useful in cDNA cloning via subtractive hybridization (Kuze, K., Shimizu, et al. (1989) Nucleic Acids Res. 17:807) and for hybrid-arrest translation (Minshull, J., et al. (1986) Nucleic Acids Res. 14:6433–6451).

The RNase H enzyme used in the above-mentioned research was isolated from *E. coli*. The *E. coli* enzyme is called "RNase HI" and is the product of the *rnhA* gene. Berkower, I., et al. (1973) *J. Biol. Chem.* 248:5914–5921; Kanaya, S., et al. (1983) *J. Biol. Chem.* 258:1276–1281. RNase H has been identified in other organisms besides *E. coli*, such as yeast, KB cells, Krebs II ascites cells and avian myeloblastosis virus infected cells, although its existence in other species is still unknown. Crouch, R. J. (1981) in *Gene Amplification and Analysis* (Chirikjian, J. G., and Papas, T. S., eds.) Vol. 2, pp. 218–228, Elseivier, North Holland, N.Y.; Crouch, R. J., et al. (1982) in *Nuclease* (Linn, S. M., and Roberts, R. J., eds.) pp. 211–241, Cold Spring Harbor Laboratory, Cold Spring Harbor, N.Y.

A thermostable RNase H would be preferable in many RNase H applications, particularly for mapping and certain diagnostic applications. In addition to the obvious advantages of longer reagent shelf life and greater stability under reaction conditions, a thermostable RNase H would allow reactions to be carried out at higher temperatures. These higher temperatures are closer to optimal temperatures for hybridization of RNA probes to target DNA and would destroy the activity of *E. coli* RNase H. The optimum temperature for a nucleic acid hybridization will depend on the hybridization buffer, but typically reaction temperatures in the 70° C. to 95° C. range facilitate maximum sensitivity by ensuring that target DNA sequences are melted and accessible and reaction temperatures in the 45° C. to 75° C. range facilitate maximum selectivity of hybrid formation because there is more hybridization stringency at higher temperature. High stringency conditions result in lower background by minimizing nonspecific binding of probes to unrelated target sequences.

What is needed in the art of molecular biology is an isolated RNase H capable of biological activity at elevated temperatures. Such an RNase H should be capable of biological activity after incubation at temperatures greater than 45° C. for at least ten minutes. Preferably the RNase H will be capable of biological activity after incubation at temperatures of at least 70° C. for at least ten minutes.

SUMMARY OF THE INVENTION

The present invention is an essentially pure preparation of thermostable RNase H obtained from *Thermus flavus*.

The present invention is also a method of digesting RNA polymers that are in duplex form with a DNA molecule. By "DNA" and "RNA" we mean naturally occurring DNA and RNA and chemically and enzymatically modified DNA and RNA. We also mean to include DNA and RNA that is synthetically made and DNA and RNA that contains variant bases. The method comprises exposing the duplex to the isolated thermostable RNase H. In a preferable form of the invention, the DNA molecule is not digested by the RNase H.

The present invention is also a genetic construct encoding a thermostable RNase H. Preferably, the construct comprises SEQ ID NO: 3 or SEQ ID NO: 4. SEQ ID NO: 3 is the sequence of thermostable RNase E obtained from *Thermus flavus*. SEQ ID NO: 4 is the sequence of a fusion protein of thermostable RNase H obtained from *Thermus thermophilus* fused to a Lac Z' N-terminal peptide.

It is an object of the present invention to provide an RNase H capable of activity at incubation temperatures close to the optimal temperatures for hybridization of RNA probes to target DNA.

It is another object of the present invention to provide an RNase H capable of activity after incubation at temperatures greater than 45° C. for at least ten minutes.

It is another object of the present invention to provide an

RNase H capable of activity after incubation at temperatures of at least 70° C. for at least ten minutes.

It is another object of the present invention to provide a method for digesting an RNA molecule when the RNA molecule is hybridized to a DNA molecule.

It is another object of the present invention to provide a genetic construct capable of producing an RNase H.

It is an advantage of the present invention that the RNase H will not become inactivated when incubated at a temperature of greater than 45° C.

It is another advantage of the present invention that the method of digesting RNA can take place at higher temperatures.

It is another advantage of the present invention that an RNase H molecule may be obtained with the use of a genetic construct.

Other objects, advantages and features of the present invention will become apparent from the following specification taken in conjunction with the accompanying drawings.

DETAILED DESCRIPTION OF THE INVENTION

1. In General.

The present invention requires an essentially pure preparation of a thermostable RNase H. By "essentially pure" we mean a preparation capable of digesting an RNA molecule when the RNA molecule is hybridized to a DNA molecule. The present invention is also a preparation of RNase H of greater than 0.01 Units/µg (units are defined below). Preferably, the preparation is greater than 1 Units/µg. This preparation should not contain substantial amounts of other enzymes or constituents that would be detrimental to the RNase H function. By "thermostable" we mean the enzyme will not lose significant biological activity after incubation over 45° C. for ten minutes. Preferably the enzyme will have significant and useful biological activity after being incubated at temperatures greater than 70° C. for ten minutes.

The existence of thermostable RNase H was previously unknown. Here, we have successfully purified a thermostable RNase H, thereby proving the existence of such an enzyme, and also described a methodology for isolation of other species of RNase H from other thermophilic organisms.

2. Purification of RNase H from a Thermostable Organism.

In order to obtain thermostable RNase H from its native host, an appropriate thermostable microorganism must be identified and cultured. Suitable microorganisms are those which contain a thermostable RNase H capable of isolation and biological activity. *Thermus thermophilus* HB8, *Thermus aquaticus* YT-1, *Thermus flavus*, and *Bacillus stereothermophilus* were discussed in the examples below, but other microorganisms are equally suitable. Organisms that are closely related to *Thermus thermophilus* HB8, such as *Thermus thermophilus* HB27, are particularly suitable. Standard fermentation methods are used to obtain a sufficient amount of the microorganism to isolate the RNase H.

Additionally, the RNase H gene may be cloned from an appropriate source, such as *Thermus thermophilus* HB8 or *Thermus flavus*, and expressed in a non-thermostable host, such as *E. coli*. Suitable quantities of the enzyme can then be produced by the heterologous host and the enzyme recovered by conventional means for recovering protein produced in such a host. Examples of a successful cloning of RNase H are given below.

A non-thermostable RNase H may be cloned and then selectively mutagenized to acquire a thermostable enzymatic activity. This could effectively be done by creating oligonucleotide sequences coding for the portions of the thermostable RNase H different from the *E. coli* enzyme and replacing those sequences in the *E. coli* RNase H gene. The resultant enzyme could then be analyzed for its ability to withstand higher incubation temperatures, such as 10 minutes at 70° C. and still function enzymatically.

The RNase H enzyme can also be isolated from other thermophilic microorganisms in an analogous procedure to the one detailed below. A first consideration is an assay for the presence of the enzyme in different purification fractions. Typically, this is done by examining a fraction for the presence of RNase H activity and a protein of the appropriate size.

The RNase digesting ability of RNase H may be detected in many ways. In the examples below, we disclose a suitable method of testing for RNase H activity. RNase H activity is assayed in a 100 µl reaction mixture containing: 1 mM poly-(rA); 100 µM oligo-(dT)$_{18}$; 0.01M Tris-HCl, pH 7.5; 10 mM MgCl$_2$, 0.1 mM EDTA; 1 mM dithiothreitol; 0.1M NaCl; and the purification fraction. The poly-(rA) and oligo-(dT) molecules will form duplexes. If RNase H is present, the poly-(rA) in the duplex will be digested and the oligo-(dT) will be free to form another duplex. Thus, the reaction will "cycle". The digested ribonucleosides are acid soluble and may be spectrophotometrically monitored. After incubation at 45° C. for 20 minutes, 1 ml of ice-cold 5% trichloroacetic acid is added to the reaction mixture. After incubation on ice for 5 minutes, the precipitate is removed by microcentrifuge centrifugation. The absorbance of the supernatant solution is determined at 260 nm in a spectrophotometer. One unit of RNase H is defined here as the amount of enzyme generating 1 nmole of acid-soluble product in 20 minutes under the above conditions.

Preferably, during the purification all initial steps are conducted at 4° C. The chromatographic steps are conducted at room temperature. Purification of RNase H is preferably monitored by sodium dodecyl sulfate polyacrylamide gel electrophoresis (SDS-PAGE). The stained electrophoretic gels are monitored for the occurrence of a protein of the appropriate size. *Thermus thermophilus* and *Thermus flavus* RNase H is approximately 20,000 d. RNases H isolated from other organisms are of comparable size. For instance, *E. coli* RNase H is approximately 17,500 d.

Preferably, 1 Kg of cells is suspended in a buffer containing 50 mM Tris-HCl, pH 7.5; 1.0 mM EDTA; 0.1% (v/v) 2-mercaptoethanol; and 5% (v/v) glycerol (abbreviated as TEBG buffer). The cells are lysed and the lysate is treated with polyethyleneimine to precipitate the nucleic acids. The lysate is centrifuged. The pellet contains nucleic acids and is discarded.

At this point, it is useful to subject the supernatant to ammonium sulfate precipitation. The protein fraction that precipitates between 33% and 45% saturation with ammonium sulfate contains RNase H. This precipitate is collected by centrifugation, dialyzed against TEBG buffer and then dialyzed against TEBG buffer additionally containing 0.05M NaCl for approximately 6 hours or until the sample is the same conductivity as the BioRex 70 chromotography buffer.

After dialysis, the solution is preferably applied to a BioRex 70 column equilibrated with TEBG/0.05M NaCl buffer. The purpose of the BioRex 70 column is to remove contaminating proteins.

The unbound protein is washed from the BioRex 70 column with the TEBG/0.05M NaCl buffer. RNase H is eluted from the column with a salt gradient of 0.05–0.5M NaCl. In the example below, a single activity peak was eluted at approximately 0.3M NaCl, but the elution point might vary from preparation to preparation. The fraction containing RNase H activity may be located by either an RNase H assay or SDS-PAGE analysis.

Fractions containing RNase H are pooled and the protein is precipitated with ammonium sulfate at 66% saturation. This precipitate is collected by centrifugation and dissolved in a small volume of TEBG buffer.

The dissolved sample is then preferably chromatographed on a Sephacryl S-100 HR sizing column. The purpose of this column procedure is to separate the proteins contained in the sample by size. Fractions are taken from this column and each fraction analyzed for RNase H activity. Protein concentration in the column fractions may be determined by a protein assay, such as the Bradford assay. Bradford, M. M. (1976) *Anal. Biochem.* 72:248–254. Fractions containing RNase H are pooled and dialyzed against TEBG/0.05 NaCl.

This pooled sample is preferably chromatographed on a heparin agarose column equilibrated with TEBG/0.05 NaCl buffer. The heparin agarose column procedure removes additional protein contaminants. Fractions are assayed for RNase H activity and aliquots are electrophoresed on SDS-PAGE. Fractions containing RNase H are pooled and dialyzed against storage buffer. The enzyme may then be stored at −20° C. A typical storage buffer is 0.05M Tris-HCl, pH 7.5; 0.1 mM EDTA; 1 mM dithiothreitol; 0.1M NaCl, 50% (v/v) glycerol; and 0.1% (v/v) Triton X-100.

3. Thermostability Analysis.

A newly isolated RNase H must be analyzed for thermostability to verify the desired level of that trait. This is most easily done in a comparison test with *E. coli* RNase H, as described below in the Examples. Basically, the new RNase H and *E. coli* RNase H are individually pre-incubated in a reaction buffer without poly-(rA) and oligo-(dT). RNase H activity is determined after adding poly-(rA) and oligo-(dT). The reaction mixture is incubated at different temperatures to determine the temperature stability range of the RNase H. In the examples below, the RNase H digestions were incubated for ten minutes at 37° C., 45° C. 70° C. and 90° C. in 50 µl of reaction buffer containing 0.01M Tris-HCl, pH 7.5, 10 mM MgCl$_2$, 0.1 mM EDTA, 1 mM dithiothreitol, and 0.1M NaCl.

After readjusting the incubation temperature back to 20° C., poly-(rA) and oligo-(dT) are added to the enzyme-containing solution and the RNase H activity determined. An RNase H is "thermostable" if after incubation at temperatures greater than 45° C. for ten minutes, the RNase H is capable of digesting the added poly-(rA). In the example below, the RNase H from *Thermus thermophilus* was incubated at 45° C. to obtain optimum digestion, as compared to 37° C. for *E. coli* RNase H.

4. Purity of Enzyme.

A single unit of RNase H activity was defined above as the amount of enzyme generating 1 nmole of acid-soluble product in 20 minutes in the assay for RNase H activity described above. By using the purification protocol generally described above, it is possible to reliably isolate thermostable RNase H in a purity such that the activity level is above 100 units per µg total protein. Since as produced in its native organism, the concentration of thermostable RNase H is less than 0.01 units per µg, this represents a concentration of the enzyme in excess of 10,000 times over its concentration in the native organism. In general, separated fractions recovered from host organisms which have activity levels in excess of 0.1–1 units per µg total protein would provide useful levels of enzyme concentrations for at least some molecular biology procedures. At a purification of 10 units per µg, still ten-fold less than is possible by our purification method, the preparation is useful for many more molecular biology procedures.

5. Obtaining a Genetic Construct Capable of Expressing RNase H.

The present invention is also a genetic construct capable of expressing RNase H. Such a construct involves two elements: The first element is a sequence encoding RNase H. The second element is a vector with appropriate regulatory sequences capable of expressing the RNase H coding sequence.

One may obtain an RNase H coding sequence by probing a library prepared from the DNA of an organism that expresses RNase H, such as *Thermus thermophilus* or *Thermus flavus*. The examples below detail successful methods of obtaining a clone in this way. In brief, one would construct a nucleic acid probe prepared from the known RNase H protein sequence (SEQ ID NO: 1) and screen the library with this probe.

Other ways to obtain an RNase H coding sequence would be known to one skilled in the art. For example, one might incubate lysed bacterial cells with an antibody which is reactive with an RNase H, such as *Thermus thermophilus* or *Thermus flavus* RNases H.

A sequence capable of expressing RNase H is inserted in an expression vector capable of promoting expression of the RNase H protein. This vector may be a plasmid or a viral vector. Suitable examples are pUC18 plasmid, pBluescript KSII phagemid or λgtll viral vector.

EXAMPLES

1. Purification of RNase H from Thermus thermophilus.

*Thermus thermophilus* HB8 strain (available without restriction from the American Type Culture Collection, 12301 Parklawn Drive, Rockville, Md. as ATCC No. 27634) was grown in a 300 liter fermenter in the following medium: 4 g/L yeast extract; 8 g/L peptone; and 2 g/L NaCl. The pH was controlled at 7.5–8.0 with ammonium hydroxide, the dissolved oxygen was maintained at 40%, the temperature was maintained at 70° C., and the stirring rate was maintained at 400 rpm. Cells were harvested by centrifugation at late log phase at a cell density of approximately 5 g/L.

RNase H activity was assayed in a 100 µl reaction mixture containing: 1 mM poly-(rA); 100 µM oligo(dT)$_{18}$; 0.01M Tris-HCl, pH 7.5; 10 mM MgCl$_2$, 0.1 mM EDTA; 1 mM dithiothreitol; 0.1M NaCl and the purification fraction. After incubation at 45° C. for 20 minutes, 1 ml of ice-cold 5% trichloroacetic acid was added to the reaction mixture. After incubation on ice for 5 minutes, the precipitate was removed by microcentrifuge centrifugation. The absorbance of the supernatant solution was determined at 260 nm in a spectrophotometer. One unit of RNase H was defined as the amount of enzyme generating 1 nmole of acid soluble product in 20 minutes under the above conditions.

Purification of RNase H was monitored by tris-glycine, sodium dodecyl sulfate polyacrylamide gel electrophoresis (abbreviated as SDS-PAGE). The gels contained 15% acrylamide with an acrylamide/bis-acrylamide ratio of 30:1. Gels were electrophoresed, stained in Coomassie brilliant blue, and destained by standard methods, Laemmli, U. K. (1970) Nature 277: 680–685. A set of polypeptides (described below) was used as a molecular weight standard.

*T. thermophilus* RNase H was purified using the following protocol. All of the purification steps were conducted at 4° C. with the exception of the chromatographic steps, which were conducted at room temperature. 1 kg of cells was suspended in a buffer consisting of 50 mM Tris-HCl, pH 7.5; 1.0 mM EDTA; 0.1% (v/v) 2-mercaptoethanol; and 5% (v/v) glycerol (abbreviated as TEBG buffer). Cells were lysed and the lysate was treated with polyethyleneimine to precipitate the nucleic acids. Jendrisak, J. (1987) in *Protein Purification* (Burgess, R. R., ed.), Alan R. Liss, Inc., New York, N.Y., pp. 75–97.

After centrifugation, the protein fraction precipitating between 33% and 45% saturation with ammonium sulfate was collected by centrifugation and was dissolved against TEBG buffer. The resulting solution was dialyzed against TEBG buffer containing 0.05M NaCl.

The dialysate was applied to a 2.5-cm×15-cm column of BioRex 70 equilibrated with TEBG buffer containing 0.05 M NaCl. After washing unbound protein from the column with the same buffer, RNase H was eluted from the column with 10 column volumes of a salt gradient of 0.05–0.50M NaCl. Fractions of approximately 20 ml were collected.

Figure 1:
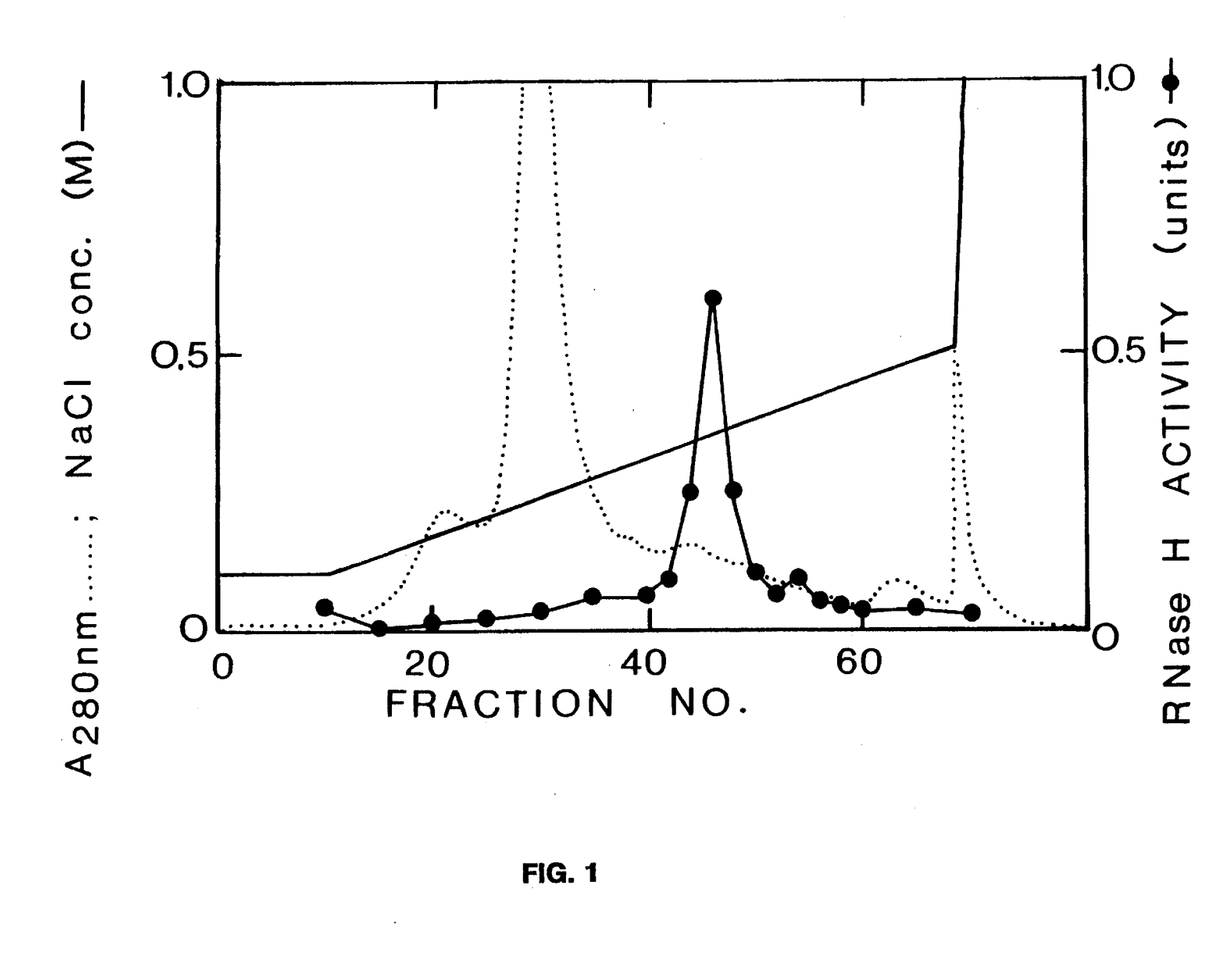
FIG. 1 is a chromatogram of *T. thermophilus* RNase H on BioRex 70.

A single activity peak was eluted at approximately 0.30M NaCl from the column. The protein was continuously monitored at 280 nm with an Isco Model UA-5 absorbance monitor. FIG. 1 is a chromatogram showing the RNase H peak. Flowthrough and wash fractions are not shown on the FIG. 1 chromatogram. 50 µl aliquots were assayed for RNase H activity. Fractions 43–49 were pooled and protein concentrated for subsequent chromatography on Sephacryl S-100 HR. 5 µl aliquots of every fifth column fraction were subjected to an SDS-PAGE analysis along with a lane of polypeptide molecular weight markers. Fractions 45–50 had a protein band at approximately 20 Kd, suggesting that RNase H was present.

Figure 2:
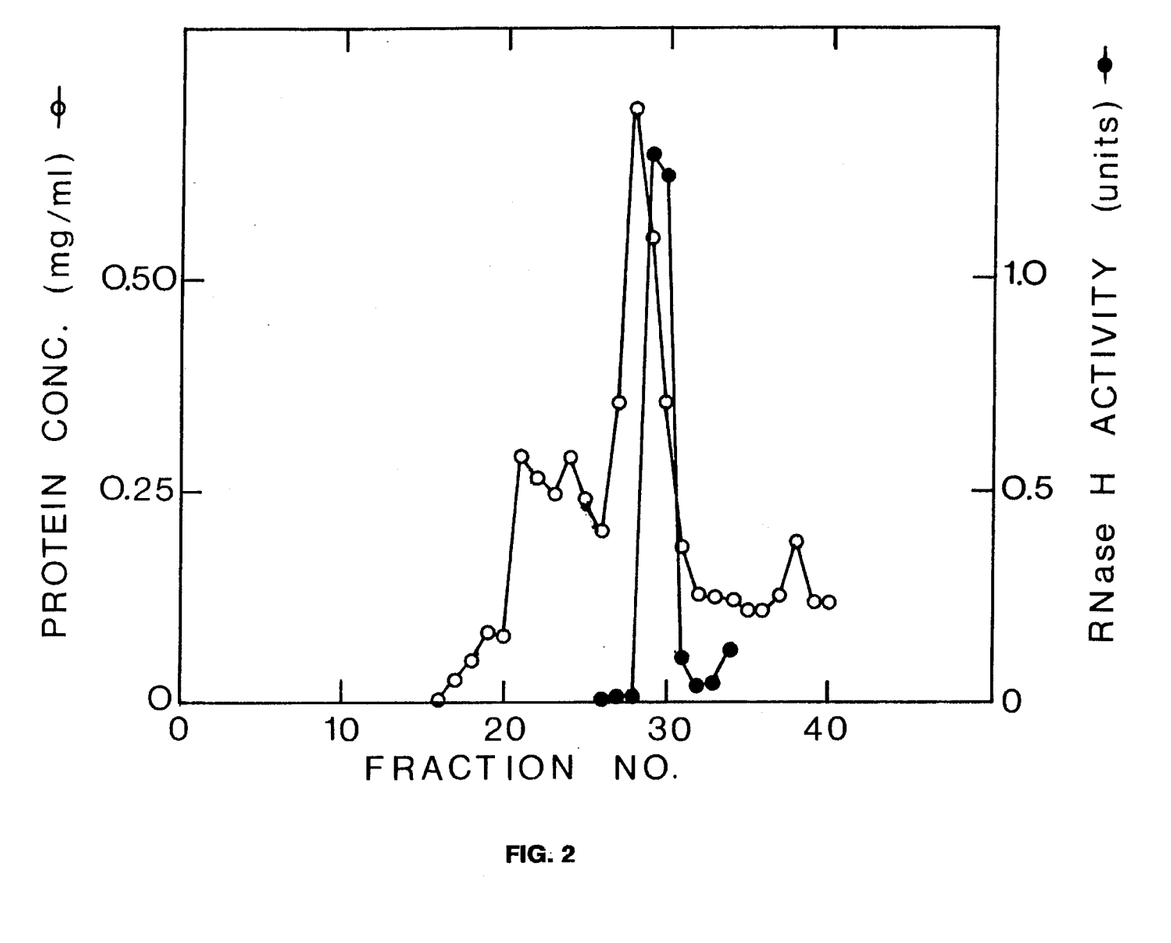
FIG. 2 is a chromatogram of *T. thermophilus* RNase H on Sephacryl 5-100 HR.

The active fractions (43–49) were pooled and the protein was precipitated with ammonium sulfate at 66% saturation. The precipitate was collected by centrifugation and was dissolved in a small volume of TEBG buffer. The protein sample was then chromatographed on a 2.5-cm×122-cm Sephacryl S-100 HR sizing column equilibrated with TEBG/ 0.5M NaCl. Fractions of approximately 20 ml were collected. A single peak of RNase H activity eluted at approximately 1.6 times the void volume of the column.

FIG. 2 is a chromatogram showing the RNase H peak. The protein concentration in the column fractions was determined by the Bradford dye-binding assay, Bradford, M. M. (1976) *Anal. Biochem.* 72:248–254, and the RNase H activity was determined with 10 µl aliquots of column fractions. RNase H activity was detected in fractions 29 and 30. These fractions were pooled for dialysis. An SDS-PAGE analysis was performed on 5 µl aliquots of fractions. Fraction 29 and 30 showed a band at 20 Kd.

Figure 3:
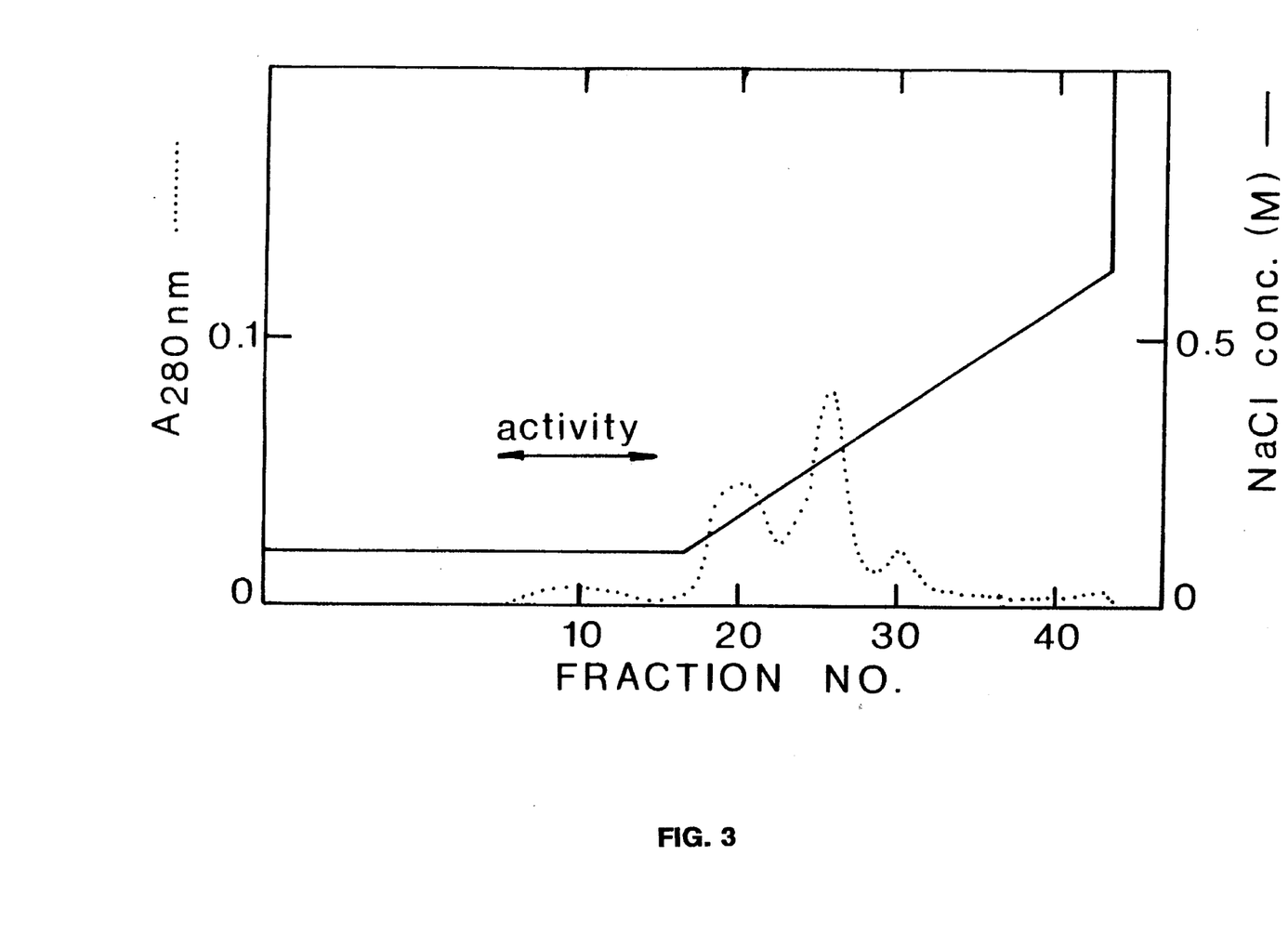
FIG. 3 is a chromatogram of *T. thermophilus* RNase H on heparin agarose.

The pooled fractions were dialyzed against TEBG buffer containing 0.05M NaCl. The sample was chromatographed on a 1.5-cm×10-cm heparin agarose column equilibrated with TEBG buffer containing 0.05M NaCl. FIG. 3 is a chromatogram that shows the results of this procedure. RNase H was eluted from the column with the same buffer and contaminants were eluted with 10 column volumes of a salt gradient of 0.05–0.25M NaCl. Fractions of approximately 4 ml were collected.

Still referring to FIG. 3, protein was continuously monitored at 280 nm with an Isco Model UA-5 absorbance monitor and RNase H activity was determined with 10 µl aliquots of column fractions as described above. Additionally, an SDS-PAGE analysis was performed on 5 µl aliquots of the heparin agarose column fractions. Fractions 8–16 contained a single polypeptide band of molecular weight 20,000 d. These fractions exactly correlated with RNase H activity in the column fractions. Fractions 7–16 were pooled and dialyzed against storage buffer prior to storage of enzyme at −20° C. The fractions were dialyzed for 16 hours at 4° C. against a storage buffer containing 0.05M Tris-HCl, pH 7.5; 0.1 mM EDTA; 1 dithiothreitol; 0.1M NaCl, 50% (v/v) glycerol; and 0.1% (v/v) Triton X-100.

2. Characterization of the Purified Enzyme.

The molecular weight of *T. thermophilus* RNase H was determined by SDS-PAGE. One µg of the protein and each marker was subjected to analysis. Marker proteins were phosphorylase b (94,000), bovine serum albumin (67,000), ovalbumin (43,000), carbonic anhydrase (30,000), soybean trypsin inhibitor (20,100), and lactalbumin (14,400). The data from the SDS-PAGE indicated that *T. thermophilus* RNase H has a molecular weight of about 20,000. This is similar to the molecular weight of *E. coli* RNase HI. *E. coli* RNase HI has a published molecular weight of 17,559 based on the derived amino acid sequence. Kanaya, S. et al. (1983) *J. Biol. Chem.* 258:1276–1281.

Amino acid analysis of the isolated RNase was performed on an Applied Biosystems 420-A-03 micro amino acid analyzer/derivatizer. Cysteine residues were first pyridylethylated after the protein was fully denatured and any disulfides reduced. The amino acid composition of *Thermus thermophilus* RNase H is presented and compared to the composition of *E. coli* RNase H in Table 1. The composition of the *E. coli* enzyme was derived from the DNA sequence of the rnh A gene. Kanaya, S. et al. (1983) *J. Biol. Chem.* 258:1276–1281. Amino acid composition indicates that the molecular weight of *Thermus thermophilus* RNase H is 20,018, which is in good agreement with the value derived from SDS-PAGE.

N-terminal microsequencing was done on the Applied Biosystems model 475 vapor phase protein sequencer. PTH-amino acids were analyzed with an on-line microbore HPLC. Data were recovered and reduced with an Applied Biosystems 900-A data workstation and sequence-dedicated software. The sequence is compared to that of *E. coli* RNase HI in Table 2 and indicates some homology, especially in a 14 amino acid block starting at residue number 12 in the *Thermus thermophilus* RNase H enzyme. Table 2 is a comparison of these segments. In Table 2, exact matches are indicated by boldface, and conservative differences are underlined. The sequence data for *E. coli* RNase HI is from Kanaya and Crouch (1983) *J. Biol. Chem.* 258:1276–1281.

TABLE 1

Amino acid composition of *Thermus thermophilus* RNase H

| Amino Acid | Abbrev. | Comp. by MW | #Residues T. thermophilus | #Residues E. coli |
|---|---|---|---|---|
| Aspartic acid + Asparagine | Asx | 13.863 | 14 | 14 |
| Glutamic acid + Glutamine | Glx | 21.715 | 22 | 20 |
| Serine | Ser | 4.820 | 5 | 4 |
| Glycine | Gly | 17.635 | 18 | 14 |
| Histidine | His | 6.273 | 6 | 5 |
| Arginine | Arg | 16.187 | 16 | 10 |
| Threonine | Thr | 7.887 | 8 | 10 |
| Alanine | Ala | 22.308 | 22 | 14 |
| Proline | Pro | 14.100 | 14 | 5 |
| Tyrosine | Tyr | 2.500 | 3 | 5 |
| Valine | Val | 7.382 | 7 | 9 |
| Methionine | Met | 3.254 | 3 | 4 |
| Cysteine | Cys | 3.622 | 4 | 3 |
| Isoleucine | Ile | 1.867 | 2 | 7 |
| Leucine | Leu | 19.596 | 20 | 12 |
| Phenylalaine | Phe | 6.965 | 7 | 2 |
| Lysine | Lys | 9.807 | 10 | 11 |

Calculated MW of sample: 20,018

TABLE 2

N-terminal amino acid sequence of *Thermus thermophilus* RNase H.

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| met | asn | pro | ser | pro | arg | lys | arg | val | ala | leu | phe | thr | asp | gly |
| met | | | | | leu | lys | gln | val | glu | ile | phe | thr | asp | gly |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| ala | cys | leu | gly | asn | pro | gly | pro | gly | gly | cys | ala | arg | leu | leu |
| ser | cys | leu | gly | asn | pro | gly | pro | gly | gly | tyr | gly | ala | ile | leu |

| 31 | 32 | 33 | 34 | | | | |
|---|---|---|---|---|---|---|---|
| arg | phe | lys | ala ... | | | *Thermus thermophilus* HB-8 | |
| arg | tyr | arg | gly ... | | | *E. coli* | |

3. Heat stability comparison of Thermus thermophilus and E. coli RNases H.

*T. thermophilus* and *E. coli* RNases H were preincubated in a reaction buffer minus poly-(rA) and oligo-(dT). The residual nuclease activities were determined after adding poly-(rA) and oligo-(dT).

10 units of *Thermus thermophilus* and *E. coli* RNases H were incubated for 10 minutes at 37° C., 45° C. 70° C. and 90° C. in 50 microliters of reaction buffer containing 0.01M Tris-HCl, pH 7.5, 10 mM $MgCl_2$; 0.1 mM EDTA, 1 mM dithiothreitol, and 0.1 M NaCl. After readjusting the incubation temperatures back to 20° C. by incubation for 10 minutes in a 20° C. water bath, 50 microliters of 2 mM poly-(rA) and 0.2 mM oligo-($dT_{18}$) in reaction buffer were added to the enzyme. After incubation for 45° C. for 20 minutes in the case of *T. thermophilus* RNase H and 37° C. for 20 minutes in the case of *E. coli* RNase H, the reactions were stopped and undigested poly-(rA) was precipitated by trichloroacetic acid precipitation. After centrifugation to pellet the undegraded poly-(rA), absorbance at 260 nm was determined for the supernatant solutions in order to determine the amount of poly-(rA) that had been digested. The absorbance values were corrected for background absorbance in a minus enzyme control and the values were normalized to the activity of *E. coli* RNase H and *Thermus thermophilus* RNase H which were not subjected to the heat treatment protocol. These values were set at 100% activity and the heat-treated activities are expressed as a percentage of these control values. The results (Table 3) indicate that *Thermus thermophilus* RNase H is stable upon heating, even up to 90° C. for 10 minutes, whereas the RNase HI from *E. coli* begins to lose activity at 45° C. for 10 minutes.

TABLE 3

Thermostability comparison of RNases H from *E. coli* and *Thermus thermophilus*

| Preincubation conditions | Residual Activity (%) E. coli | Residual Activity (%) T. thermophilus |
|---|---|---|
| 10 min., 37° C. | 100 | 100 |
| 10 min., 45° C. | 98 | 101 |
| 10 min., 70° C. | 8 | 98 |
| 10 min., 90° C. | 0 | 97 |

4. Purification of RNase H from Thermus flavus.

Figure 4:
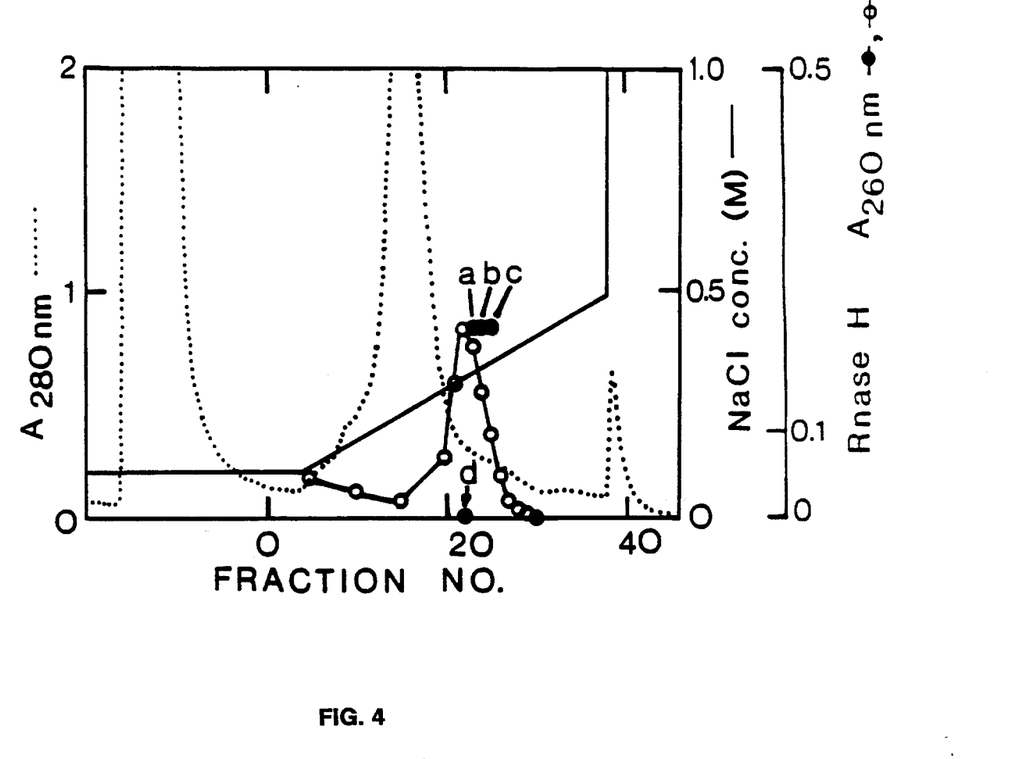
FIG. 4 is a chromatogram of *T. flavus* RNase H on BioRex 70.

*Thermus flavus* AT-62 was obtained from the American Type Culture Collection, Rockville, Md., at Accession No. 3. The strain was grown in liquid culture at 70° C. as described above for the growth of *Thermus thermophilus* HB-8. A protein extract was prepared from the thermophilic organism *Thermus flavus* as described above for *Thermus Thermophilus* and subjected to BioRex 70 column chromatography as described above. Fractions were assayed for RNase H activity. The elution profile is shown in FIG. 4. As with *Thermus thermophilus*, a single peak of RNase H activity was detected eluting at about 0.30M NaCl from the BioRex 70 column. The peak fraction was reassayed after preincubating aliquots of the peak fraction for 10 minutes at (A) 45° C., (B) 70° C. and (C) 90° C., as described in Table 3, and the residual RNase H activity was determined. At all pretreatment temperature conditions, the RNase H activity from *T. flavus* was stable and thus resembled the thermostable RNase H activity isolated from *Thermus thermophilus* HB8. The point labelled "d" in FIG. 4 is the RNase H activity when the assay was done in the absence of 100 μM oligo-(dT). The lack of poly-(A) digestion under these conditions confirms that this activity is indeed RNase H.

Figure 5:
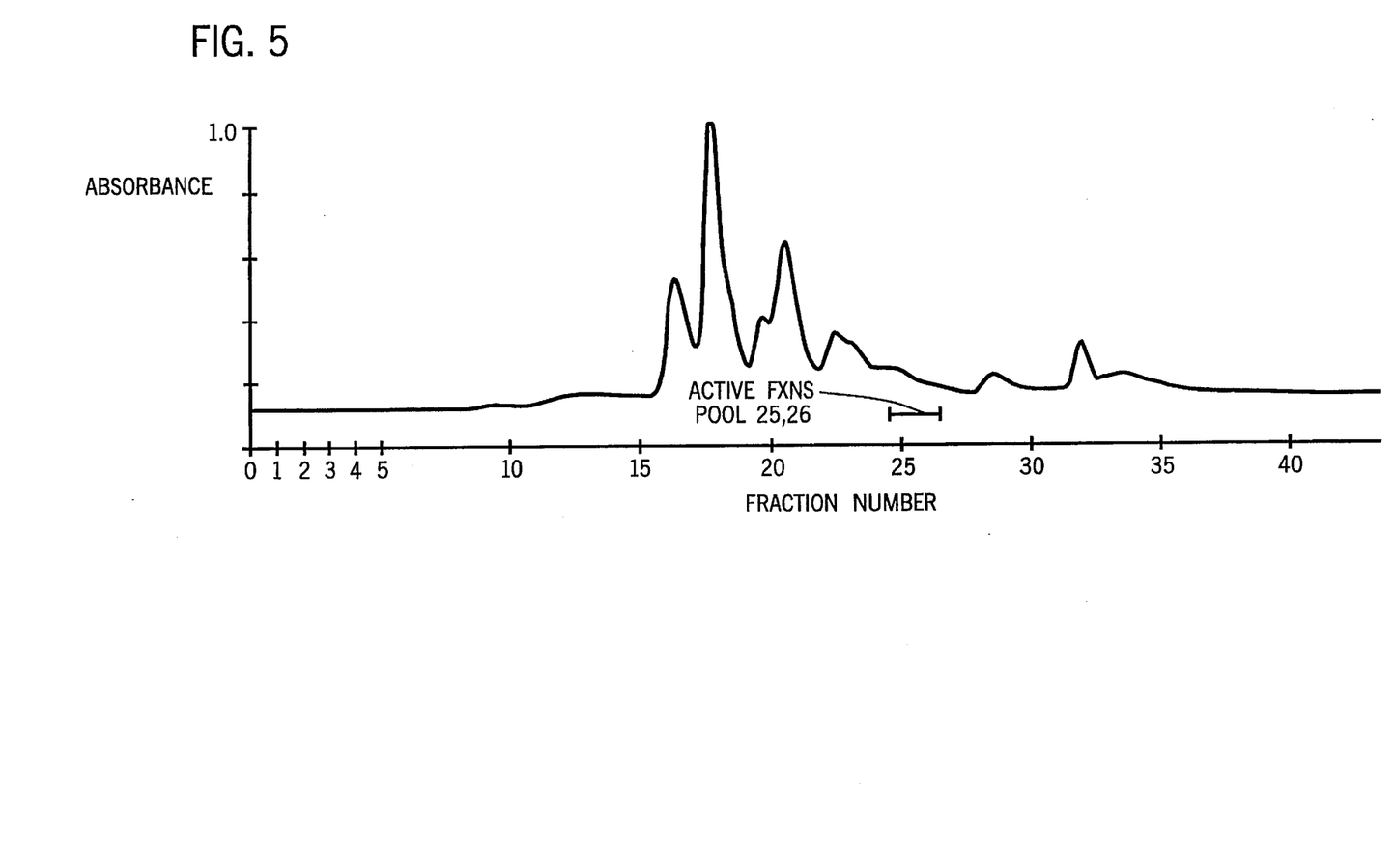
FIG. 5 is a chromotogram of *T. flavus* RNase H on Sephacryl 5-100 HR.
Figure 6:
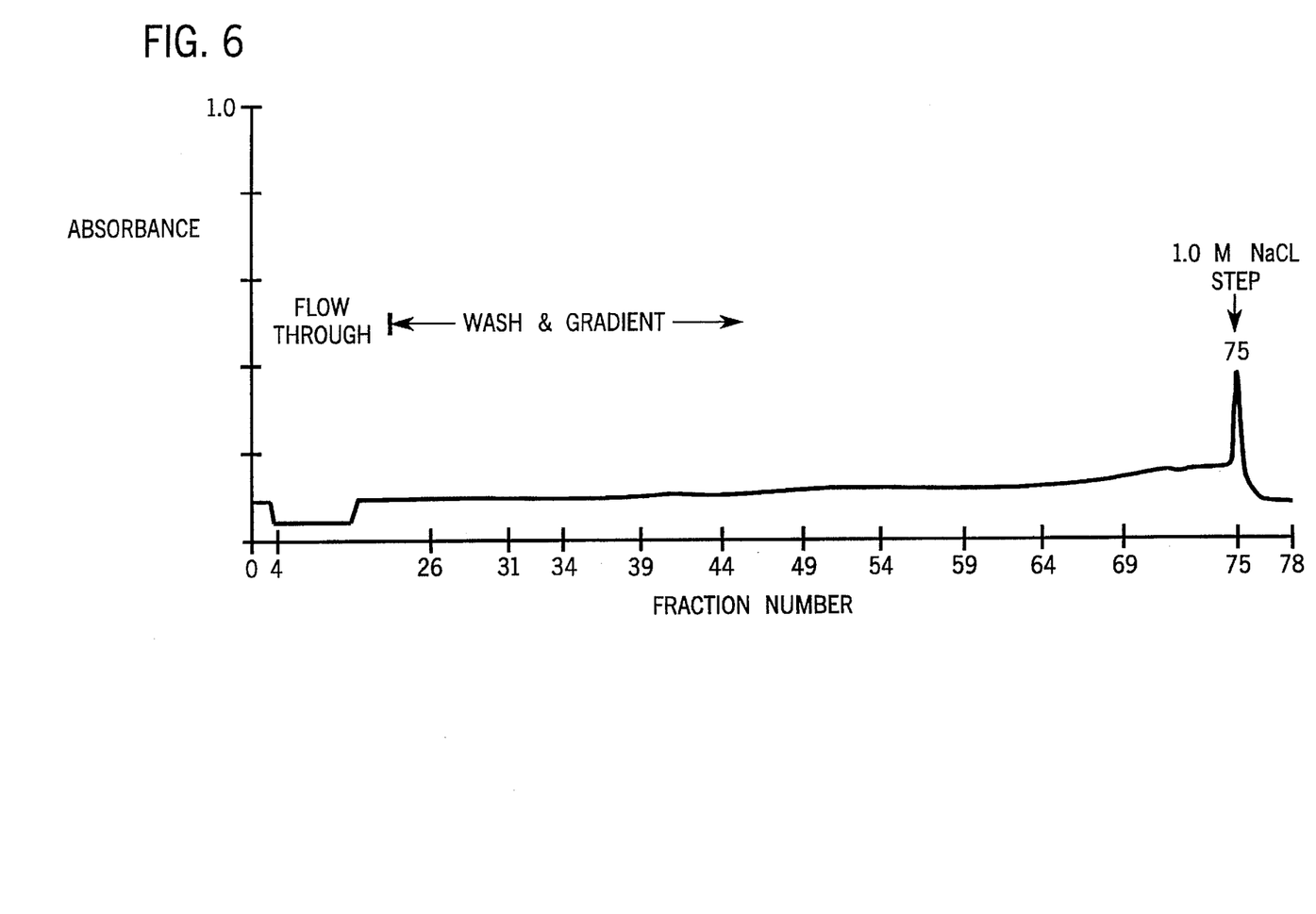
FIG. 6 is a chromotogram of *T. flavus* RNase H on heparin agarose.

Purification of the *Thermus flavus* enzyme proceeded identically to that described above for RNase H from *Thermus thermophilus*. FIGS. 5 and 6 describe the chromatography on Sephacryl S-100 and heparin agarose. The resulting positive fraction was examined on an SDS polyacrylamide gel which indicated that the enzyme was essentially free of contaminating proteins and was of approximately the same molecular weight as the *Thermus thermophilus* enzyme (20,000 d). Similar enzymatic properties to the *Thermus thermophilus* enzyme were also observed.

5. Cloning of RNase H.

A. Thermus thermophilus.

A cloned insert of *Thermus thermophilus* RNase H was originally isolated from a 7 Kb BamHI fragment inserted into a pBluescribe KSII vector (Stratagene). The 7 Kb fragment was obtained from a library of *Thermus thermophilus* DNA fragments created by SaU3A partial digestion of bacterial DNA that was then inserted into a pUC19 vector. The fragment was detected by screening with a probe obtained from the RNase H protein sequence. The fragment containing the *Thermus thermophilus* RNase H gene was further defined by recloning in a pBluescribe KSII vector as a 1.4 Kb XhoI, BamHI fragment. The *Thermus thermophilus* RNase H gene was cloned into pUC18 for expression as a fusion protein by cloning an approximately 800 bp Sau3A fragment into the BamHI site of pUC18.

The insert was sequenced and identified as RNase H by comparison with a known protein sequence for RNase H.

The expressed protein was visualized as a 23,000d fusion protein of approximately the expected size by a 13% SDS-polyamylamide gel stained with Coomasie billiant blue. In contrast, a pUC18 vector control lacking the RNase H cloned gene did not yield a similar 23,000 d protein.

To confirm the presence of a unique 23,000 d protein that has the properties of *Thermus thermophilus* RNase H, the expressed protein was resolved on a 13% polyamylamide gel, blotted onto a nylon membrane and reacted with a rabbit antibody made to native *Thermus thermophilus* RNase H following a Western blotting procedure. The *Thermus thermophilus* RNase H antibody was previously incubated with a mixture of native and denatured *E. coli* proteins bound to Sepharose-4B to remove any antibodies directed against *E. coli* proteins. The resulting preadsorbed antibody was shown to react strongly to native *Thermus thermophilus* RNase H but not to *E. coli* RNase H on a Western blot. The Western blot of cloned *Thermus thermophilus* RNase H expressed in *E. coli* showed a unique stained bond migrating as a 23,000 d protein which reacted strongly with the preabsorbed *Thermus thermophilus* RNase H antibody, whereas a pUC18 vector control which lacked the cloned RNase H did not yield a similar band.

An RNase H activity assay was performed on an *E. coli* lysate containing the cloned *Thermus thermophilus* RNase H gene and a similar lysate containing the pUC18 control vector but lacking the RNase H gene. The lysates were first treated by heating for 30 min, 70° C. to inactivate any endogenous *E. coli* RNase H, then clarified by centrifugation to remove the bulk of contaminating *E. coli* proteins. The clarified lysates were incubated with an M13 DNA/RNA hybrid where the RNA strand was labeled with $^3$H-ATP. Samples were incubated 10 min, 70° in 0.1 ml reactions. The remaining radiolabled RNA was then precipitated by the addition of 1 ml of 5% trichloracetic acid. The resulting samples were transferred to glass fiber filters for scintillation counting. The results showed that a negligible amount of $^3$H-RNA was solubilized by incubation with *E. coli* lysate lacking the *Thermus thermophilus* RNase H gene, whereas greater than 95% of the $^3$H-RNA was rendered soluble by digestion with *E. coli* lysate containing Thermus thermophilus RNase H.

*Thermus thermophilus* RNase H expressed as a fusion with the Lac Z' leader sequence of pUC18 showed a clear advantage over expression of *Thermus thermophilus* RNase H as a native protein in *E. coli* in terms of yield of RNase H produced. (SEQ ID NO: 4 is the nucleic acid sequence of the *Thermus thermophilus* RNase H sequence and the Lac Z' N-terminal peptide.) The recombinant *Thermus thermophilus* RNase H fusion protein was further purified by procedures similar to the native *Thermus thermophilus* RNase H. The purified preparations of the *Thermus thermophilus* RNase H fusion showed similar properties of size and activity as assays of heat treated lysates.

B. Thermus flavus.

A cloned insert of *Thermus flavus* RNase H (7–8 Kb) was originally isolated from a Sau3A partial digestion of bacterial DNA that was inserted into a pUC19 vector. The fragment containing the *Thermus flavus* RNase H gene was further defined by recloning in a pBluescribe KSII vector as a 1.4 Kb XhoI, BamHI fragment. The *Thermus flavus* RNase H gene can be further cloned for expression as a fusion protein, for example, by cloning a Sau3A fragment containing the gene into a pUC18 vector.

SEQ ID NO: 3 is the sequence of the *Thermus flavus* RNase H obtained from the 1.4 Kb XhoI, BamHI fragment. The sequence of the *Thermus flavus* RNase H differs from the sequence of the *Thermus thermophilus* RNase H at one position, position 486 of the coding sequence.

We envision that *Thermus flavus* RNase H expression will also be improved by expressing a fusion protein, as described above for *Thermus thermophilus*.

---

We claim:

1. An essentially pure preparation of RNase H isolated from *Thermus flavus*, the RNase H having the characteristic of being thermostable,
    wherein the RNase H has a molecular weight of approximately 20,000 daltons, is capable of digesting added poly (rA) after incubation at 70° C. for 10 minutes, and wherein the digestive capability after incubation at 70° C. for 10 minutes is at least about 98% of the digestive capability after incubation at 37° C. for 10 minutes.

2. A process of digesting RNA in an RNA-containing molecule, wherein the RNA molecule is in duplex form with a DNA molecule, comprising exposing the nucleic acid duplex under conditions suitable for enzymatic activity to an effective amount of an essentially pure preparation of a thermostable RNase H isolated from *Thermus flavus* such that the RNA is digested, wherein the RNase has a molecular weight of approximately 20,000 daltons, is capable of digesting added poly-(rA) after incubation at 70 C. for ten minutes and wherein the digestive capability after incubation at 70 C. for 10 minutes is at least about 98% of the digestive capability after incubation at 37 C. for 10 minutes.

\* \* \* \* \*